United States Patent [19]

Yannas et al.

[11] Patent Number: 4,522,753

[45] Date of Patent: Jun. 11, 1985

[54] METHOD FOR PRESERVING POROSITY IN POROUS MATERIALS

[75] Inventors: Ioannis V. Yannas, Newton Center; John F. Burke, Belmont, both of Mass.; Peter J. Stasikelis, Houston, Tex.

[73] Assignee: Massachusetts Institute of Technology, Cambridge, Mass.

[21] Appl. No.: 287,930

[22] Filed: Jul. 29, 1981

Related U.S. Application Data

[63] Continuation-in-part of Ser. No. 169,897, Jul. 17, 1980, abandoned.

[51] Int. Cl.$^3$ .............................................. B29D 27/00
[52] U.S. Cl. .................................. 260/123.7; 264/28; 264/49; 264/101
[58] Field of Search .......................... 264/28, 49, 101; 260/123.7

[56] References Cited

U.S. PATENT DOCUMENTS

| | | | |
|---|---|---|---|
| 2,610,625 | 9/1952 | Sifferd et al. ................... | 106/122 X |
| 2,712,672 | 7/1955 | Calcagno .......................... | 264/49 X |
| 2,893,102 | 7/1959 | Maxwell et al. ................. | 264/28 |
| 3,081,181 | 3/1963 | Rutenberg et al. .............. | 264/28 X |
| 3,136,682 | 6/1964 | Tu ...................................... | 264/28 X |
| 3,157,524 | 11/1964 | Artandi ............................. | 264/49 X |
| 3,368,911 | 2/1968 | Kuntz et al. ...................... | 106/155 |
| 3,428,584 | 2/1969 | Riley ................................. | 264/49 X |
| 3,471,598 | 10/1969 | Battista ............................. | 264/28 |
| 3,551,535 | 12/1970 | Henderson et al. ............. | 264/28 |
| 3,607,753 | 9/1971 | Suchoff ............................. | 264/28 X |
| 3,632,371 | 1/1972 | Mikulka ........................... | 264/113 X |
| 3,665,061 | 5/1972 | Eberly, Jr. ........................ | 264/49 |
| 3,812,224 | 5/1974 | Smith et al. ...................... | 264/28 |
| 4,060,081 | 11/1977 | Yannas et al. .................... | 128/156 |
| 4,193,813 | 3/1980 | Chvapil ............................. | 264/28 X |
| 4,279,812 | 7/1981 | Cioca ................................. | 260/123.7 |
| 4,412,947 | 11/1983 | Cioca ................................. | 260/123.7 |
| 4,440,680 | 4/1984 | Cioca ................................. | 260/123.7 |
| 4,451,397 | 5/1984 | Huc et al. ......................... | 260/123.7 |

OTHER PUBLICATIONS

Yannas, I. V. and A. V. Tobolsky, "Cross-Linking of Gelatine by Dehydration", (Reprinted from *Nature*, vol. 215, No. 5100, Jul. 29, 1967, pp. 509–510).

Yannas, I. V., and A. V. Tobolsky, "Stress Relaxation of Anhydrous Gelatin Rubbers", In *Journal of Applied Polymer Science*, vol. 12, pp. 1–8 (1968).

Chvapil, Milos; Richard L. Kronenthal; and Walton van Winkle, Jr., "Medical and Surgical Applications of Collagen", in *International Review of Connective Tissue Research*, vol. 6, Edited by D. A. Hall and D. S. Jackson, New York, Academic Press (1973), pp. 1–61.

Chvapil, M., J. A. Owen and D. S. Clark and S. Koorajian and A. P. Goodman, "Effect of Collagen Crosslinking on the Rate of Resorption of Implanted Collagen Tubing in Rabbits", in *J. Biomed. Mater. Res.*, vol. II, pp. 297–314 (1977).

Chvapil, Milos, "Collagen Sponge: Theory and Practice of Medical Applications", in *J. Biomed. Mater. Res.*, vol. II, pp. 721–741 (1977).

Stasikelis, Peter Joseph, "Burn Dressings Based on Collagens Structural Parameters Affecting Performance", M. S. Thesis, Mechanical Engineering Department, MIT, May 1979, 120 pages.

"Hackh's Chemical Dictionary", Fourth Edition, completely revised and edited by Julius Grant, New York, McGraw-Hill, ©1972, pp. 685, 705.

*Primary Examiner*—Philip Anderson
*Attorney, Agent, or Firm*—Arthur A. Smith, Jr.; David E. Brook

[57] ABSTRACT

A method for preserving the porosity of porous materials is disclosed. In this method, the porous material is subjected to elevated temperature and vacuum conditions to thereby produce a dimensionally-stable, non-collapsible porous material.

8 Claims, No Drawings

METHOD FOR PRESERVING POROSITY IN POROUS MATERIALS

GOVERNMENT SUPPORT

The invention described herein was made in the course of or under grants from the National Institutes of Health.

RELATED APPLICATION

This application is a continuation-in-part of U.S. application Ser. No. 169,897, filed on July 17, 1980, now abandoned.

DESCRIPTION

1. Field of the Invention

This invention is in the field of materials and more particularly relates to the treatment of porous materials to preserve their porosity.

2. Background of the Invention

Many materials are formed to contain a large number of pores. For example, certain materials or nonwoven materials are porous, as are a large number of foams based upon natural or synthetic polymers. In many applications for such porous materials, it is important for the porous material to retain its porosity during exposure of the material to liquids without collapse of the pores.

One example of materials where this is true is a new class of tissue-compatible materials which are also insoluble in the presence of body fluids and controllably degradable in the presence of body enzymes and has been disclosed in commonly assigned U.S. Ser. No. 030,183 filed Apr. 16, 1979 now U.S. Pat. No. 4,280,904. These materials are known as crosslinked collagen-mucopolysaccharide composites. They are synthesized by intimately contacting collagen with a mucopolysaccharide and subsequently crosslinking the resulting product. Suitable collagens can be derived from a number of animal sources, and suitable mucopolysaccharides include, but are not limited to, chondroitin 4-sulfate, chondroitin 6-sulfate, dermatan sulfate, keratan sulfate, heparan sulfate, heparin, and hyaluronic acid. Insolublization can be achieved by chemical, radiation, or other suitable crosslinking techniques, or dehydrothermal treatment. Dehydrothermal treatment is particularly preferred and is achieved by reducing the moisture level of the composites to a very low level, such as by subjecting the composite material to elevated temperatures and high vacuum.

These crosslinked collagen-mucopolysaccharide composites are believed to be comprised of collagen molecules or collagen fibrils with long mucopolysaccharide chains attached to them. Crosslinking appears to anchor the mucopolysaccharide chains to the collagen so they will not elute or otherwise become disengaged.

These crosslinked collagen-mucopolysaccharide composites have been found to retain the advantageous properties of native collagen. Additionally, such materials can be synthesized to be very weakly antigenic, degradable by collagenase or other enzymes at controllable rates, and insoluble in the presence of body fluids. Additionally, such composites can be synthesized to have ultimate tensile strengths, elongations at break, and other mechanical properties particularly desired for artificial skin grafts and wound dressings.

These crosslinked collagen-mucopolysaccharide composites have been combined with moisture transmission control layers adherently bonded thereto to form synthetic skin. The moisture transmission control layers are formed from nontoxic materials which control moisture flux of the overall membrane and can be formed from synthetic polymers such as silicone resins, polyacrylate or polymethacrylate esters or their copolymers, and polyurethanes. Such synthetic skin is described in U.S. Pat. No. 4,060,081, issued to Yannas et al., on Nov. 29, 1977; the teachings of this patent are hereby incorporated by reference.

In many applications for the crosslinked collagen-mucopolysaccharide composites, it has been found highly preferable to prepare these materials as highly porous foams. For example, in the use of these materials as medical prostheses, including their use as synthetic skin, there is frequently a need for migration of cells from adjacent host tissue into the prosthesis. Such migration provides firmer attachment of the prostheses to the tissue and is also indispensable whenever there is a requirement for the invading cells to synthesize new functional tissue inside the pores of the prosthesis, which, if biodegradable, eventually disappears from the original site leaving in its place the newly synthesized tissue. In short, it has been found that high porosity in these composite materials, very often in excess of 90% pore volume, allows a significantly greater degree of cell infiltration, elicits a much reduced fibrous sac, and allows desired tissue synthesis to occur at a much faster rate than corresponding material produced as membranes without high porosity.

Despite the need for porous materials, most traditional technqiues for producing foams are not suitable to produce materials which are biocompatible. For example, it is well known to produce foamed solids by employing blowing agents to produce synthetic polymeric foams. An example of the use of blowing agents is the formation of polyurethane foams. However, the preparation of such foamed polyurethanes generally involves the use of toxic chemicals, such as diisocyanates, which may often remain in an incompletely reacted form. This would be particularly objectionable in the case of a collagen or collagen-mucopolysaccharide based material, which would evoke little or no inflammatory response itself, but would generate a toxic inflammatory response if unreacted diisocyante were present. It is also difficult to control foam density or porosity using blowing agents, and even when possible it requires elaborate processing steps including addition of catalytic systems which also may be toxic.

Because of the problems with conventional foam generation techniques, it has been found preferable to produce porous materials based upon crosslinked collagen mucopolysaccharide composites by a technique known as freeze drying. In this technique, an aqueous dispersion of the composite is quickly frozen and the resulting ice particles are subsequently caused to sublime in the presence of vacuum. A solid, highly porous material results, and the degree of porosity can be controlled by adjusting the concentration of solids in the dispersion prior to the rapid freezing, as well as by adjusting the temperature and vacuum to which the drying membrane is exposed during the process.

Although the freeze drying technique has been found to be generally suitable, the materials produced do suffer one disadvantage. This disadvantage is that the dry porous solids obtained by sublimation of ice under vacuum often shrink considerably and irreversibly when brought into contact with liquids, such as an aqueous solution. Such shrinkage causes closure of the pores and makes the material less useful in the applications where the high level of porosity is required or preferable. Unfortunately, most applications for these porous biocompatible materials require that the material be further processed or stored in aqueous solutions, or require that the materials be placed in contact with aqueous body fluids during use, which would also cause undesirable shrinkage of a prosthesis formed from such materials.

The problems of shrinkage and pore collapse suffered by porous crosslinked collagen-mucopolysaccharide materials are illustrative of problems encountered with porous materials based upon a wide variety of natural and synthetic polymers when such porous materials are brought into contact with liquids.

DISCLOSURE OF THE INVENTION

This invention relates to the treatment of porous materials, particularly highly porous materials (e.g., above 90% pore volume) with a combination of elevated temperature and vacuum to modify such materials so that their porosity is preserved when they are subsequently contacted with fluids.

In one embodiment, the invention contemplates the production of dimensionally-stable, non-collapsible protein materials. Such materials are produced by forming an aqueous dispersion of protein. The aqueous dispersion is then quickly frozen to form ice particles, which are subsequently sublimed to produce a highly porous protein foam. The foam is subjected to elevated temperature and vacuum conditions sufficient to produce the dimensionally-stable, non-collapsible protein foam.

An important advantage is the degree of control over the porosity of the resulting protein foams which can be gained. Porosity, for example, can be controlled by adjustment of the solids content of the dispersion prior to the quick freezing step as well as by adjustment of the temperature and pressure employed during the freeze-drying process.

Porosity is preserved, even upon contact with liquids, by the treatment under elevated temperature and vacuum. This prevents shrinkage of the foam materials when they are subsequently contacted with liquids during further processing, storage or use. This is especially advantageous since the most common methods of crosslinking collagen involve contacting it with an aqueous solution of a crosslinking agent, such as glutaraldehyde. Without prior dehydrothermal treatment, it would be very difficult to crosslink the collagen without damaging its porosity. In addition, one preferred method of storing the collagen membrane described in U.S. Pat. No. 4,060,081 (Yannas et al, 1977) is in the hydrated form, in a sterile watertight pouch that contains a piece of membrane immersed in a saline solution.

One class of materials suitable for production of porous protein foams is the class of crosslinked collagen-mucopolysaccharide composite materials described above. However, protein foams can be formed from pure collagen or other proteins in their pure form, such as gelatin, albumin, fibrinogen, and soybean protein. Additionally, collagen or these other protein molecules can be grafted with various comonomers to form composite or grafted protein foams.

The initial step in preparation of these protein foams is the formation of an aqueous dispersion of the protein. Collagen-based material can be employed by first swelling the collagen in aqueous acidic medium. In this regard, it is particularly preferred to swell collagen at a low pH, such as about 3.5 or lower. See, examples 16 and 17 of Ser. No. 030,183, filed Apr. 16, 1979, the teachings of which are hereby incorporated by reference.

Control over porosity of the foams can be achieved at the dispersion stage by adjusting the solid content of the dispersion. In general, higher porosity will be attained as the solids content is lowered. Additionally, control of porosity can be obtained by adjusting the temperature and vacuum during freeze-drying.

In regard to producing shaped articles from the dispersions of protein, there are several alternative methods which may be employed. In one method, the aqueous dispersion is simply filtered to produce porous sheets which can subsequently be shaped. On the other hand, more intricate shapes, such as are often required to produce arterial or venous tubing, can be produced by a crossflow filtration molding method described in commonly assigned U.S. Ser. No. 029,229, filed Apr. 11, 1979, now U.S. Pat. No. 4,252,759.

Porosity is achieved by freeze drying techniques which generally involve subjecting the shaped article to low temperatures, so that ice crystals are formed, followed by sublimation of the ice under vacuum. Such techniques are known to those skilled in the art and many of these have been described in the patent literature. See, for example, U.S. Pat. Nos. 3,632,371; 3,471,598; 3,368,911; and 2,610,625.

The shaped protein foams are treated under high temperature and vacuum. In general, temperatures of 80° C. to 180° C. have been found suitable for collagen based foams. The vacuum may vary from about 1 mtorr up to slight vacuum just below atmospheric pressure. Practical combinations of temperatures and pressures for collagen based materials have been found to be 80° C. at 50 mtorr, 105° C. at 1 torr and 150° C. at 600 torr. An increase in temperature or vacuum can be used singly or in combination to accelerate the process of pore preservation.

As mentioned above, a particularly important use for the highly porous protein foams produced by the method described herein is in multilayer membranes useful to cover wound dressing. Thus, wound dressings or synthetic skin can be produced by multilayer membrane formed from either collagen or crosslinked collagen-mucopolysaccharide composite used in conjunction with moisture transmission control layers as described in U.S. Pat. No. 4,060,081.

When used as synthetic skin, the multilayer membrane described in U.S. Pat. No. 4,060,081 exhibits two very beneficial characteristics that result from very high porosity. First, if the porosity of the collagen material exceeds about 90%, and is preferably about 95% to 98%, then epithelial cells tend to grow between the collagen layer and the silicone layer. Since the collagen layer must be covered by epithelial cells before it can be biodegraded and the wound fully closed, this is very desirable. Second, if the porosity is sufficiently high to encourage epithelial cell growth between the collagen layer and the silicone layer, then the silicone layer is spontaneously ejected soon after the wound is fully covered by neoepidermal skin. This eliminates the need for cutting, peeling, or any other delicate or invasive procedures to remove the silicone layer.

Of course, porous materials can be produced which are based upon other polymers, including natural polymers such as cellulose and synthetic polymers which do not flow under elevated temperatures. Another protein which can be employed is leather, including ground leather obtained from leather scrap. A porous foam containing ground leather could be particularly useful as acoustic and/or thermal insulation.

Porosity can be achieved by any known technique, such as by forming a foam employing a blowing agent. As mentioned above, freeze-drying is often the preferred method for preparing foams of biocompatible materials.

This invention can be further and more specifically illustrated by the following example.

EXAMPLE 1

Bovine hide collagen in pulverized form (0.55 g) was dispersed in 200 ml of 0.05M acetic in a refrigerated Eberbach blender over 1 hour. Chrondroitin 6-sulfate (0.044 g) was dissolved in 40 ml of 0.05M acetic acid and the solution was added dropwise to the stirred collagen dispersions. After 10 min of additional homogenization the blender was stopped and the dispersion was poured into a 250 ml plastic centrifuge bottle and was centrifuged for 1 hour at 2200 rpm at 4° C. in an International Model PR-1 centrifuge. Following centrifugation, 140 ml were decanted from the bottle and the concentrate was blended for 15 min. 65 ml of the dispersion was poured into a shallow aluminum pan, $18 \times 5 \times 8.5$ cm, which was placed on the shelf, maintained at $-55°$ C., of a Virtis 10 LN freeze drying chamber for 1 hour.

The frozen dispersion was then freeze dried to the point where no ice formed on the condenser coils of the chamber. The dry foam was placed in a vacuum oven maintained at 105° C., pressure 60 mtorr, for 12 hours. After allowing for 30 minutes of cooling the foam was covered with a 15-mil thick layer of room-temperature-curing silicone rubber medical adhesive (Dow Silastic). It was then immediately placed in 0.05M acetic acid at 4° C. for 48 hours to re-swell. The swollen membrane was then immersed in 200 ml of 0.25% glutaraldehyde in 0.05M acetic acid for 24 hours at 20° C., rinsed thoroughly with water and stored in 70/30 isopropanol/water until ready for use as a closure for full-thickness skin wounds.

When prepared in this manner, the membrane exhibits very high porosity when studied by a scanning electron microscope. For example, pore volume fractions in the range of 90-98% have been routinely determined by use of techniques well known to users of light and electron microscopes. The average value of pore diameter in these membranes has ranged from about 5 $\mu$m to about 300 $\mu$m.

In the absence of the heat-treatment step under vacuum following freeze drying, these membranes were observed to shrink, when immersed in an aqueous medium, (e.g., 70/30 isopropanol/water) to about one-fourth or less of their original dimensions and to have irreversibly lost their porosity, as shown by scanning electron microscopy.

EXAMPLE 2

A total of approximately 11 membranes, prepared as described in Example 1 with variations to determine the effects of specific parameters, were grafted onto skin wounds on female Hartley guinea pigs. The typical skin wounds were $1.5 \times 3$ cm, and were produced by removing the entire epidermis and dermis to the panniculus carnosus. Each membrane was carefully draped across the wound, sutured into place, and covered with a bandage. After varying periods of time, some of the animals were sacrificed and cross sectional slices of the graft were removed and studied. Histological analyses indicated that collagen lattice porosity in excess of about 90% tends to encourage rapid cell growth and migration within the lattice, and that porosity of about 95% or higher tends to promote epithelial cell growth between the collagen lattice and the silicone layer. Other grafted wounds were allowed to heal completely. It was observed that epithelial cell growth between the collagen lattice and the silicone layer tends to cause the silicone layer to be spontaneously ejected soon after the neoepidermal layer closes the wound. This eliminates the need for peeling or surgically removing the silicone layer from the wound.

Industrial Utility

The porous protein foams produced by this invention have utility in medical and surgical application requiring films, membranes, sutures, or other prostheses which are biocompatible and porous. They are also believed to have utility as protein component in many foodstuffs. Other porous materials, such as non-woven materials, have use as fabrics, leather substitutes, etc.

Equivalents

Those skilled in the art will recognize, or be able to ascertain employing no more than routine experimentation, many equivalents to the specific materials, steps, etc., described above. Such equivalents are intended to be covered by the following claims.

We claim:
1. A method of producing dimensionally-stable, non-collapsible highly porous foams based upon insoluble protein-based material, comprising:
   a. forming a liquid dispersion of said insoluble protein-based material;
   b. quickly freezing said dispersion to form frozen liquid particles;
   c. subliming said frozen liquid particles to produce a highly porous foam;
   d. subjecting said highly porous foam to an elevated temperature of from about 80° C. to about 180° C. and vacuum of from about 1 mtorr to just below atmospheric pressure, said temperature and vacuum conditions being sufficient to stabilize said highly porous foam so that its porosity is preserved when it is contacted with a liquid solution of a chemical crosslinking agent, and,
   e. subjecting said stabilized highly porous foam to a liquid solution of a chemical crosslinking agent so as to produce a dimensionally-stable, non-collapsible highly porous foam material.

2. A method of claim 1 wherein said liquid dispersion comprises an aqueous dispersion.

3. A method of claim 2 wherein said insoluble protein-based material comprises a crosslinked collagen-mucopoly-saccharide composite material.

4. A method of claim 2 wherein said insoluble protein-based material comprises ground leather.

5. A method of claim 3 wherein said highly porous foam comprises a foam of greater than about 95% porosity.

6. A highly porous foam material produced by the method of claim 1.

7. A highly porous foam material produced by the method of claim 5.

8. In the production of a multi-layer membrane having a first layer formed from a protein-based polymer and a second layer comprising a moisture transmission control layer, the improvement wherein said first layer comprises a highly porous foam material based upon insoluble protein-based material having a porosity of greater than about 95% which has been subjected to an elevated temperature of from about 80° C. to about 180° C. and vacuum of from about 1 mtorr to just below atmospheric pressure in order to preserve its porosity and subsequently contacted with an aqueous solution of a chemical crosslinking agent to to cause said highly porous foam to become dimensionally-stable and non-collapsible.

* * * * *